United States Patent
Nicholas

(10) Patent No.: US 9,664,634 B2
(45) Date of Patent: May 30, 2017

(54) NANOSTRUCTURED SENSOR ARCHITECTURE AND METHOD FOR ENHANCED CHEMICAL DETECTION

(71) Applicant: NanoLab, Inc., Waltham, MA (US)

(72) Inventor: Nolan Walker Nicholas, Worcester, MA (US)

(73) Assignee: NanoLab, Inc., Waltham, MA (US)

( * ) Notice: Subject to any disclaimer, the term of this patent is extended or adjusted under 35 U.S.C. 154(b) by 96 days.

(21) Appl. No.: 14/831,503

(22) Filed: Aug. 20, 2015

(65) Prior Publication Data

US 2016/0054258 A1    Feb. 25, 2016

Related U.S. Application Data

(60) Provisional application No. 62/039,511, filed on Aug. 20, 2014.

(51) Int. Cl.

| | | |
|---|---|---|
| *G01N 27/403* | (2006.01) | |
| *G01N 27/12* | (2006.01) | |
| *G01N 27/327* | (2006.01) | |
| B82Y 30/00 | (2011.01) | |
| *G01N 27/22* | (2006.01) | |
| *G01N 27/06* | (2006.01) | |

(52) U.S. Cl.
CPC ............ *G01N 27/127* (2013.01); *B82Y 30/00* (2013.01); *G01N 27/3278* (2013.01); *G01N 27/06* (2013.01); *G01N 27/227* (2013.01); *G01N 2027/222* (2013.01)

(58) Field of Classification Search
CPC .. G01N 27/3278; G01N 27/227; G01N 27/06; G01N 27/128; G01N 27/22; G01N 27/221; G01N 2027/222; G01N 27/414
See application file for complete search history.

(56) References Cited

U.S. PATENT DOCUMENTS

| | | | | |
|---|---|---|---|---|
| 5,747,839 A | * | 5/1998 | Hammond | ........... G01N 27/414 257/252 |
| 2011/0045466 A1 | * | 2/2011 | Lin | ..................... C12Q 1/6804 435/29 |

FOREIGN PATENT DOCUMENTS

DE            10201006224 A1 *   5/2012    ........... G01N 27/414

OTHER PUBLICATIONS

WIPO computer-generated Englsih language translation of DE 102010062224 A1, patent published May 31, 2012.*

* cited by examiner

*Primary Examiner* — Alexander Noguerola
(74) *Attorney, Agent, or Firm* — Pandiscio & Pandiscio

(57) ABSTRACT

Apparatus for detecting and identifying a chemical species in an environment, the apparatus comprising: a plurality of carbon nanotubes arranged to form a network, the network comprising a plurality of inter-carbon nanotube junctions; a plurality of electrical contacts, each of the plurality of electrical contacts being connected to the network such that the anisotropic electrical characteristics of the network can be measured dynamically while the network is exposed to the environment; wherein the network possesses electrical anisotrophy such that the ratio of the number of inter-carbon nanotube junctions which must be traversed by current per length of the plurality of carbon nanotubes differs for different directions within the network along the path from one of the plurality of electrical contacts to another of the plurality of electrical contacts, and further wherein the electrical anisotrophy of the network changes when a chemical species is present in the environment.

2 Claims, 6 Drawing Sheets

FIG. 2A   FIG. 2B

(AVERAGE ELECTRIC DIRECTION FIELD THROUGH VANTA STRUCTURE)

NANOSTRUCTURED SENSOR ARCHITECTURE AND METHOD FOR ENHANCED CHEMICAL DETECTION

REFERENCE TO PENDING PRIOR PATENT APPLICATION

This patent application claims benefit of pending prior U.S. Provisional Patent Application Ser. No. 62/039,511, filed Aug. 20, 2014 by NanoLab, Inc. and Nolan Walker Nicholas for NANOSTRUCTURED SENSOR ARCHITECTURE AND METHOD FOR ENHANCED CHEMICAL DETECTION, which patent application is hereby incorporated herein by reference.

FIELD OF THE INVENTION

This invention relates to carbon nanotubes (CNTs) in general, and more particularly to novel sensors comprising carbon nanotubes which can be used for detecting a chemical species.

BACKGROUND OF THE INVENTION

Section 1

Detection of chemical species is an on-going need for many scientific, medical, and technological applications. Nano-structured sensor architectures have been widely utilized for enabling chemical detection due to their large surface-to-volume ratios and sensitivity to surface chemical environments. High aspect ratio structures such as 1D nanowires and 2D sheets have provided particular usefulness in the creation of electronic read-out sensors. Carbon nanotubes (CNTs) have been demonstrated in the prior art as effective sensor materials for chemical species and have been utilized to detect a wide range of chemical species in several different sensor methodologies including chemiresistive measurements on CNT networks, CNT field emitters for breakdown ionizaton gas detectors and electrochemical detectors on CNT-based electrodes. (However, it remains a desirable technical goal for sensor systems to be able to both detect and distinguish a variety of chemical species utilizing a simple, compact sensing architecture.

SUMMARY OF THE INVENTION

Section 2

In this invention are disclosed a materials and device architecture and an associated method of use for enabling the detection and identification of chemical species:

Comprising: A plurality of CNTs arranged to form a network (or plurality of networks) such that said network (or networks) possess electrical anisotropy such that the ratio of the number of inter-CNT junctions which must be traversed by current per length of CNT differs for different directions within the network along the path from one electrical contact to another electrical contact.

In an embodiment this may be achieved via a network architecture that has in at least two orthogonal directions (axes) a different number per unit length of the junctions between nanotubes, which in turn gives rise to electrical anisotropy along each axis and comprising a plurality of electrical contacts (at least three) connected to said network such that the anisotropic electrical characteristics of the system can be measured dynamically while subjected to the influence of environmental stimuli (e.g. the presence of chemical species).

(*wherein the aforementioned "paths" are implicitly defined with reference to current flow between the various electrodes)

A method for measurement comprising the application of a series of electrical signals to the CNT network through the electrical contacts wherein said electrical signals are applied across various paths of the electrical contacts and wherein secondary modulator influencers may be applied during measurement to enable enhanced measurement efficacy and selectivity.

Section 3

In this sensor technology, multiple degrees-of-freedom of the electronic network properties are measured by this method and parameterized with regard to frequency, voltage and secondary influencers (e.g. illumination). In this case, the primary electronic properties are both resistances and reactances measured along two anisotropically different network paths where the network path containing more CNT-to-CNT junctions is referred to as the "transverse" path ($R_\perp X_\perp$) whereas the network path containing fewer CNT-to-CNT junctions is referred to as the "parallel" path ($R_\parallel, X_\parallel$). This correlation of multiple degrees-of-freedom provides means for sensitive detection and identification of a broad range of chemical species and mixtures thereof.

This technology combines a plurality of sensing mechanisms within a single device architecture and technique to enable detection and distinguishment of a wide range of chemical species. The sensor technology/methodology/device taught herein interacts with a plurality of the various intrinsic properties associated with any molecular species. This enables the detector to be both sensitive and selective in sensing and distinguishing a plurality of chemical species based on a combination of properties characteristic to each chemical species. Such intrinsic properties include HOMO/LUMO states, molecular shape & size, bond polarizations and orbital/bond polarizabilities, electron pair donicity/acceptance, et cetera and provide specific interaction characteristics with the sensor architecture described herein. Thereby the sensor technology taught herein combines a plurality of traditional sensing mechanisms known in the art such as chemiresistive, chemicapacitive (including both DOS and electrostatic effects) and point-contact measurement techniques within a single nanomaterials architecture and thus improved performance as a detector by enabling detection and identification of a wide variety of chemical species and of multiple species simultaneously.

As is well known in the art, every chemical species intrinsically possesses physico-chemical properties, so that when chemical species are suitably proximate to (e.g. adsorbed onto, absorbed onto, or in other near proximity) the CNT network then they can interact with and affect the electronic characteristics of said CNT-network. For instance chemical species which donate electrons to the CNTs may create chemical contact doping effects which affect the conductivity along the CNT axis; in contrast chemical species which are polarizable and/or enable electron "hopping" transport will impact properties such as the lateral capacitive reactance and junction resistance of the CNT network—particularly when absorbed at/near a lateral junction. Additionally, many chemical species will adsorb differently along the CNT length versus near CNT-CNT junctions. This invention surpasses previous technologies in that it enables the simultaneous measurement of a plurality of these physico-chemical properties and allows both the detection and identification of a plurality of species. Below is a partial list enumerating some of the relevant physico-chemical characteristics which contribute to sensing by the type of measurement device taught herein:

Contact potential & contact doping (e.g. electron pair donor molecules are known to strongly interact with carbon nanotubes and to modify their electronic structure)

Molecular Polarizability (due both to orientable molecular bond polarization&orbital/bond polarizability)

Out-of-plane carrier scattering and transfer through and in the presence of adsorbed chemical species (e.g. tunneling current, hopping/leakage current)

Non-symmetric electrical potentials can be applied to the contacts, under suitable circumstances different modes of transport (e.g. tunneling vs. hopping) may often respond differently to these signals (e.g. momentum & energy matching criterion will be different)

Tunneling vs. Hopping modes may also be differentiated as a function of secondary applied influencers such as temperature, illumination and magnetic field In-plane Carrier Scattering—adsorption of various species is known to affect the mean free path (scattering length) of charge carriers within carbon nanotubes which affects the internal resistance of the carbon nanotubes. Additionally, certain molecular adsorption effects will sometimes differentially affect the carrier mobility of one carrier type with respect to another (holes vs. electrons). Carrier differentiated scattering can be measured by methods known in the art such as application of a magnetic field to produce a hall effect (which produces an out-of-plane scattering).

Internal modes
(vibrational/rotational/electronic energy levels)—available internal energy states and the population thereof will in general affect the electronic impact of the molecules (e.g. polarizability, electron transfer processes, etc.) furthermore information regarding these modes can be spectroscopically probed by illuminating the sensor architecture with wavelength selected light during electronic impedance measurements.

Adsorption/Desorption energy—the energy of binding for a particular chemical species to the surface of the CNT provides significant information about the chemical identity of the species and can be probed by inputting energy into the adsorbed species (e.g. by heating, spectrally selective illumination, or pressure modulation) while taking a series of impedance measurements. Furthermore, it is common that different species will differentially bind to different types of sites within a CNT network (e.g. at a junction vs. an open sidewall)—which will each contribute differentially to electronic measurements of the type taught herein

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 2A, 2B and 2C are schematic views showing an exemplary device architecture with capacitive coupling, formed in accordance with the present invention;

DETAILED DESCRIPTION OF THE PREFERRED EMBODIMENTS

Section 4

Explanatory Embodiment 1

Figure 1A:
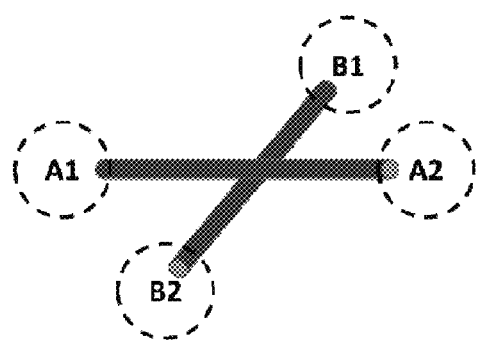
FIGS. 1A, 1B and 1C are schematic views showing carbon nanotubes arranged together to form a simple cross shape.
Figure 1B:
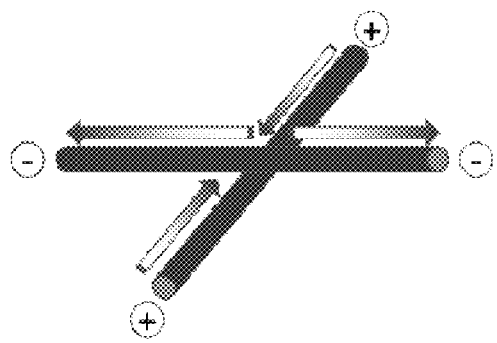
Figure 1C:
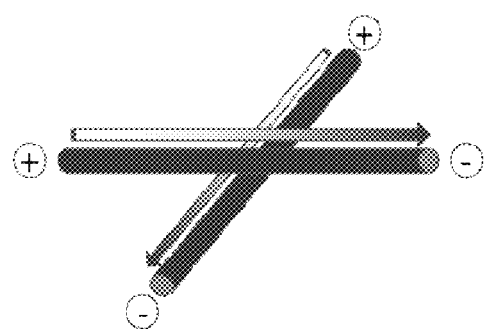

As a basic example, a simple electrical network consisting of two carbon nanotubes (nanotube A and nanotube B) arranged together to form a simple cross shape is illustrated in FIG. 1. By applying various potential differences between the various ends of the nanotubes (labeled as A1, B1, A2, B2) differentiated paths with anisotropic electrical characteristics can be measured as illustrated in FIGS. 1B and 1C. For example in FIG. 1B, if the nanotube ends A1 & A2 are held at an equivalent positive potential versus nanotube ends B1 & B2, then current will flow from A1 & A2 to B1 & B2 while traversing one intra-CNT junction. In contrast, as in FIG. 1C, if A1 & B1 are held at an equivalent positive potential versus A2 & B2 then current will flow from A1 to A2 and B1 to B2 and traverse an essentially equivalent length of CNT but without traversing an intra-CNT junction. By varying the frequency and potential of the electrical signals which are applied to these contacts and measuring the resulting output, the effective electrical characteristics both along the lengths of the nanotubes and through the inter-CNT junction can be measured. These characteristics are a sensitive indicator of the type and identities and concentration of chemical species present. In addition, the electrodes may be polarized in a nonsymmetrical fashion (e.g. A1>A2>B1=B2), which can alter the dynamics of inter-CNT charge transfer across the junction and intra-CNT scattering from the junction (e.g. tunneling vs. hopping charge transfer) which can be further utilized to identify characteristics of the chemical environment.

This device and accompanying method enables the measurement of multiple linearly independent parametric variables which by inter-correlation of these signals enables detection and identification of multiple different chemical species and mixtures thereof.

$$\check{Z}_\parallel(f,V,\xi_i, \ldots ,\xi_n) \text{ and } \check{Z}_\perp(f,V,\xi_i, \ldots ,\xi_n)$$

This may be simply embodied as illustrated in FIGS. 2A & 2B by placing aligned nanotubes onto a substrate in a "Crossed" configuration and making electrical contact to the ends of the carbon nanotubes. In some embodiments, this contact can be made without physical contact (e.g. via a capacitive coupling), which can simplify the reliable fabrication of suitable contacts.

Such a device architecture with capacitive couplings is illustrated in FIGS. 2A & 2B. As a simple extension, a device may also be constructed from a plurality of crossed carbon nanotubes, which possesses the advantage of providing a plurality of nanotube junction points which can provide stochastic insensitivity to the particular idiosyncratic details of the physical form of each individual junction point. It is noteworthy that FIG. 2B shows a relatively small number of carbon nanotubes; in some embodiments the number of carbon nanotubes used to form such a junction will be relatively large.

Figure 2C:
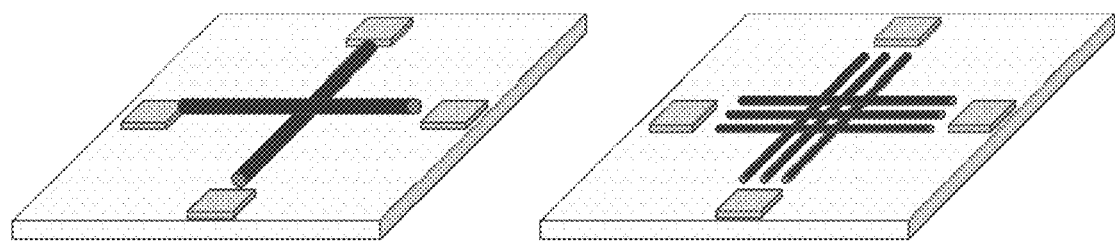
Figure 2C:
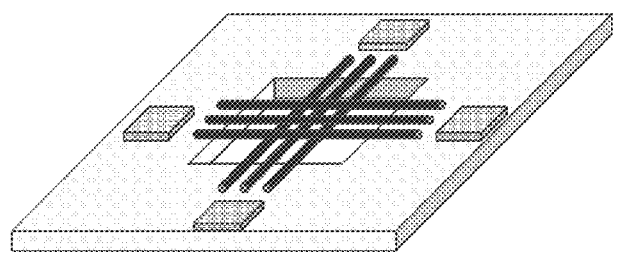

In some cases the CNT architecture may be supported on a substrate which is constructed to enable analyte to flow directly through the CNT sensor architecture as shown in FIG. 2C.

Section 5

Test Parameters

This technology enables direct electrical measurements of the anisotropic components of both real and imaginary parts of the impedance CNT network for each set of measurement parameters (e.g. frequency, applied potential, secondary influencers, etc.). This provides at least four datapoint values for each parameter test set.

$$\tilde{Z}_{\|}(f,V,\xi_i,\ldots,\xi_n) \text{ and } \tilde{Z}_{\perp}(f,V,\xi_i,\ldots,\xi_n)$$

Section 5A

Primary Test Parameters

The primary test parameters are the applied potentials at each contact point, and the signal frequency. In some embodiments these may be applied as constants (i.e. "pure" waveforms) for each data point measurement. In other embodiments, the applied potentials and frequency may be applied in a non "pure" waveform (e.g. as wavelets). Both the applied potential and the frequency will probe the transport dynamics of carriers within the network which are affected by the type of chemical species present in suitable proximity to the structure of the network. For instance, various charge transport and conduction processes along the CNTs (e.g. ballistic, diffusive) and across the CNT junctions (e.g. hopping, tunneling, capacitive coupling) possess different scaling relationships vs. applied voltage and frequency. In some embodiments frequency may be applied between the range of ~10 Hz to ~100 MHz.

In certain embodiments, correlated electrical signals may be applied along multiple directions within the CNT network at once—termed "crossed potentials." Due to the nature of charge transport within the nanoscopic CNT structure, charge transport in one direction can also affect the dynamics of charge transport in another direction (e.g. the amount of current flowing along the length of the nanotube may alter the effective resistance of charge transport across inter-CNT junctions). In certain embodiments, electrical signals may be applied such that a high-frequency electrical signal may be superimposed on top of a much lower frequency electrical signal. In such embodiments the superimposition of high-frequency atop of an effective bias offset can be utilized to resolve transport dynamics effects (e.g. capacitive reactance & junction resistance) resulting from the chemical environment of the CNT network sensor.

Section 5B

Secondary Test Parameters ("Influencers")

In addition to the primary electrical parameters described above, a variety of secondary "influencers" may be applied to the sensing device contemporaneously to the electrical measurement which can enable and/or enhance further sensing and identification of chemical species present.

Temperature: Modulation of temperature of the CNT network will modulate both the electrical carrier dynamics (including carrier populations and thermally activated transport) and also adsorption characteristics of chemical species onto the surface of the CNTs (both at junction sites and along the CNT length). Temperature modulation can be achieved by a variety of methods including thermal conduction of heating of a substrate in contact with the CNT network, electrical current heating of the CNT network by imposed current, radiant heating by an illumination source, etc. (The Vertically Aligned carbon NanoTube Array ("VANTA") architecture is advantageous for this in that it has a very high ratio of thermal conductivity to thermal mass—thus enabling rapid cycling of spatially quasi-isothermal conditions.)

Pressure: Modulation of local pressure, and/or gas partial pressure can be utilized to alter the interaction of environmental chemical species with the carbon nanotube network (e.g. by altering the thermodynamic and/or kinetic equilibrium of adsorption of chemical species to the CNT architecture). This can be utilized to further distinguish chemical information, since the shift will affect different species differently (e.g. due to differences in adsorption/desorption binding and activation energies). In one embodiment, pressure may be modulated dynamically during measurement (e.g. sinusoidally) with a well-defined relationship to the time-varying potential of the electrical measurement so that sensing information may be extracted in the frequency domain. In one embodiment this pressure shift may be achieved by enclosing the sensor architecture within a cell comprising one wall (preferably the wall opposite the CNT sensor network) which is an electrically actuated membrane.

Light: Illumination of CNT networks in the presence of adsorbant species may be utilized to modulate the effect produced by the presence of these species on the electrical signal of the device via three mechanisms separately or in combination. Illumination may be continuous or time-modulated (e.g. pulsed). The utilization of time modulated illumination (e.g. one which bears a synchronized temporal relationship to the applied electrical signal) can be utilized to provide relevant information in the frequency domain to improve measurement characteristics. It is of note that these techniques are broadly applicable to other nanostructured sensor architectures as appropriate to the sensor geometry.

Illumination may be utilized to drive desorption (including selective desorption) of chemical species from the CNT network. E.g. illumination of the CNTs by broad-band thermal radiation. In certain embodiments it may be advantageous to drive desorption by illuminating the CNT network during with a light source of periodically varying intensity (e.g. such that the light is applied primarily during the low bias periods of the electrical test signal).

Spectrally selected illumination may be utilized to modulate the state of particular molecules (e.g. bond vibrations, electron shell occupancy, etc.) and thus modify the resultant electronic signal generated by adsorbed chemical species. In cases where a sensitizer is utilized, illumination may be selected in such a way as to activate the sensitizer species and/or adsorbant/sensitizer complexes. In some embodiments this illumination will be applied as a periodically modulated source synced to the applied electrical test signal—e.g. the illumination may be applied to coincide with the peak applied electrical potential.

Suitable illumination may be utilized to modulate carrier populations within the CNT network (e.g. by generating excitons).

Suitable illumination may be utilized to modulate non-carrier quanta populations within the CNTs (e.g. plasmons, phonons, etc.) which can be utilized to influence charge transport within the CNT network (e.g. via hopping & scattering processes).

The polarization of incident illumination can be utilized to selectively affect the transport characteristics probed by the illuminated CNT network. E.g. light may be polarized in alignment with or normal to the CNT axes and junctions to selectively probe different transport characteristics and effects of the chemical environment. It will be recognized by those skilled in the art that a great variety of polarization geometries may be chosen advantageously depending upon the geometry of the CNT network, and the chemical characteristics which are of interest.

In some embodiments, it may be advantageous to couple oscillating illumination with oscillating pressure modulation. E.g. device can be constructed such that illumination, pressure, and electrical bias are all applied at the same frequency so that the network is illuminated maximally during the minimal pressure & electrical bias portion of the cycle (which are simultaneous) in order to selectively debind undesirable species.

Magnetic field: Magnetic fields applied perpendicular to the conduction path of carriers within the CNT network can be utilized to generate Hall effect transport. By utilizing the differentiated impact that many molecular adsorbants on different types of charge carriers (electrons versus holes), Hall effect transport can be utilized to further contribute to differentiated sensing of chemical species by the CNT network device.

Biasing voltage: In the presence of a conductive media (e.g. electrolyte solution), a secondary bias may be applied to the overall CNT network relative to a counter electrode (in addition to electrical signals applied across the CNT network). This bias can be utilized to modulate the concentration of charged and polarizable species within the solution to the vicinity of the CNT network, thus enabling the selective modulation of chemical species contributions to electronic signals measured by the device.

Alternatively, in the presence of a secondary electrode interface (e.g. for a CNT network film atop a dielectric film backed by a conductive material), a bias may be applied between the CNT film and the backing electrode as described in the prior art and may be utilized e.g. to modify the carrier population within the CNTs and thus enhance detection of particular doping effects from various analytes. In a particular embodiment, horizontally aligned carbon nanotube architectures (e.g. "VANTA ribbons") are useful for enabling this type of architecture as structures which can more significantly affected by this mechanism. In some embodiments this backing electrode may be constructed in the form of a circuit which possesses significant inductance to reduce signal contributions to the resistive/capacitive signal from the backing electrode.

CNT Network Structure Modification: Modification of the geometrical architecture of the CNT network can be utilized to alter the electrical properties of the CNT network (e.g. altering the ratio of capacitive vs. resistive lateral reactance). For instance compression of a VANTA architecture along the axis of the CNTs in the film or perpendicular to the axis of the CNTs in the film, can be utilized to dynamically modify its internal architecture and commensurate electrical properties. This can be utilized to alter the sensor response of the CNT network to analytes.

CNT Network Sensitization: Deposition of a known chemical species onto the surface area of the CNT network can be utilized to modulate the response of the network to other species and thereby enable and/or enhance the selective detection of chemical species by the device.

In typical preferred embodiments the action of the sensitizer (e.g. binding to a counter-part chemical species) will be reversible to enable ongoing use of the sensor. E.g. binding of HCl by a weak Lewis base adsorbed to the CNT network would typically be easily reversible whereas binding of oxygen by a phosphine species would not.

In some embodiments, the sensitization may be introduced to the CNT network via a dynamic method, in other embodiments the sensitization incorporated into the CNT network as a static component of the device.

Dynamic sensitizers are species which can be introduced into the sensing volume (e.g. mixed into the test gas stream) during a test period which act to modulate the effect that another chemical species has on the measurement operation of the device. For instance, incorporation of volatile gases and vapors such as $NH_3$, $SO_3$, $H_2SO_4$, $B(OCH_3)_3$, etc. can be utilized as Lewis acid-base species to selectively bind to counterpart species (adduct formation) or counterbalance the effect of certain chemical species and thereby alter the output signal of the device.

Static sensitizers are species which are incorporated into the CNT network architecture and reside there as a permanent part of the device architecture. A variety of static sensitizers are considered in this teaching.

Chemical species which adhere non-covalently to the CNT network and which will not debind under standard operational conditions may be utilized as static sensitizer materials for suitable analytes.

Examples of such species include:

Individual molecules with sufficiently low vapor pressures, e.g. porphyrins

Polymeric species (including oligomers, DNA, etc.) which may be utilized to bind selectively to analyte species, interfere with the signal produced by analyte species, or prevent the diffusion of particular analyte/interferent species to the CNT surface (e.g. by hydrogen bonding interactions or steric hindrance). E.g. ultrathin polymeric layers may be swelled by exposure to VOCs while the thinness of the layer can enable very rapid adsorption/desorption cycling of sensing events.

Nanoparticles may be utilized as static sensitizers to decorate the surface of the CNT network to provide selective interactions with analyte species.

The atomic lattice of the CNTs forming the network may be doped (e.g. by the incorporation of non-carbon atoms)—thus leading to altered electrical characteristics of the CNT network and differentiated responses to some analyte species.

The CNT network may be chemically functionalized by covalently bound surface groups (e.g. hydroxyl, carboxyl, dichloromethyl, etc.) which can be utilized to selectively alter the interaction of the CNT network with various analyte species.

Section 6

Preferred Embodiments

In a preferred embodiment, the CNT network may be constructed in the form of a "Vertically Aligned Array," and herein will be referred to as a VANTA (Vertically Aligned Nanotube Array). Vertically aligned array architectures, also sometimes referred to as a "forest" or "carpet" in the literature, may take several forms and are generally characterized by a large number of carbon nanotubes which are anchored to the substrate on one end and extend generally vertically along their length (normal to the plane of the substrate). However, for the purposes of this technology, we consider VANTA architectures wherein the vertical alignment is not absolute and rather that the VANTA architecture intrinsically contains a large number of lateral, side-to-side contacts between nanotubes along their length. Being that this type of VANTA architecture creates a highly anisotropic network that contains a substantial presence of inter-CNT junctions, this type of VANTA is well suited to embodiment of the architecture described herein. These type of VANTA architectures can be produced directly from a suitably constructed CVD process as is well described in the literature. (Herein, where the term VANTA is used without other clarification it will be presumed to refer to this type of VANTA architecture.) In addition, it is noteworthy that other quasi-one-dimensional nano-objects such as metal and semiconductor nanowires can also form similar architectures which can also be utilized instead-of or in conjunction with carbon nanotube architectures to embody this the sensor technology disclosed herein.

The VANTA architecture is well-suited to embody this technology due to its intrinsic high anisotropy, very large surface area for adsorption, high electrical conductivity, and low volumentric density enabling efficient diffusion of species within it. This architecture provides various sites including both free-length and junction sites where chemical species can adsorb and affect the electrical characteristics of the network. The VANTA architecture provides a stochastically constructed architecture with a very large plurality of CNTs and junctions—this enables measurements based upon stochastically averaged geometric characteristics rather than individual, atomically precise constructions which are often difficult to reliably reproduce.

Specifically, multiple electronic contacts are made to the VANTA so that these contacts enable the imposition/application of voltage differentials (current paths) both parallel to the long axis of the CNTs (normal to the plane of the substrate) and also enable application of voltage differentials transverse to the axis of the carbon nanotubes (parallel to the plane of the substrate). By applying input signals along both vertical and transverse directions across a range of input frequencies the (anisotropic) resistive and reactive electronic properties of the VANTA architecture can be distinctly measured.

In this embodiment, this technology comprises a device and method to detect and characterize the presence of chemical species containing the following elements (various embodiments may utilize all elements or some sub-set):

An volume of electrically conducting nano-objects assembled into a VANTA-type architecture
  in a preferred embodiment these nanotubes will be of small diameter (e.g. SWNT, DWNT, or FWNT). DWNT are particularly useful in that they possess few walls (and are thus highly sensitive to effects from adsorption of species to the outer wall and are also radially stiffened which restricts flattening of side-to-side junctions and improves the junction geometry for adsorption and sensing of chemical species
  in some embodiments multiple different VANTA-type architecture elements may be utilized in parallel (e.g. a CNT VANTA and a gold nanowire VANTA) to provide additional discrimination signal to distinguish and characterize various chemical species
  in some embodiments the CNT utilized may be include CNTs which encapsulate other materials (e.g. CNTs which encapsulate TiC).
  in a preferred embodiment the VANTA architecture will be supported on a non-conducting substrate
  in some embodiments it may be advantageous to use nanoarchitectures which are distinct from the above description of the VANTA architecture but provide functionally similar geometry—e.g. it is known that VANTAs may be converted into thin strips or ribbons adhered horizontally along a substrate while maintaining a similar, anisotropic internal architecture A plurality of electrical couplings to the VANTA architecture such that the electrical impedance characteristics of the VANTA architecture may be measured over a suitable range of conditions (frequency, direction, etc.)
  In a preferred embodiment electrical couplings will be configured to measure anisotropic impedance characteristics of the VANTA architecture by utilizing contact geometries which enable current flow both parallel to the axis of the nanotubes and transverse to the axis of the nanotubes
  In a preferred embodiment these couplings may be capacitive—this eliminates difficulties in forming suitable ohmic contacts to CNT materials and VANTA architectures
  In other embodiments, one or more of the electrical contacts may be made directly to the VANTA architecture to enable very low frequency measurements and to enable the average potential of the VANTA architecture to be modified (e.g. for use in liquid environments)

A system to control the introduction of chemical samples (gas or liquid) the sensor architecture for analysis. Such a system may contain elements to determine the sample amount presented to the sensor system, and may often contain sorbents to remove expected interferences as is common in the art.

Electronic system capable of supplying electrical signal across the various electrical couplings over a range of frequencies and input signal amplitudes (e.g. voltages) and capable of measuring and analyzing the signal output resulting from these electrical inputs.

Additional species included within the VANTA architecture (e.g. physisorbed onto the VANTA) to enhance sensitivity and discrimination for particular chemical species.

Secondary control apparatus to provide additional controls, functionality, sensitivity, and discrimination for usage of the VANTA architecture for chemical detection.

Particular Embodiment

Figure 3A:
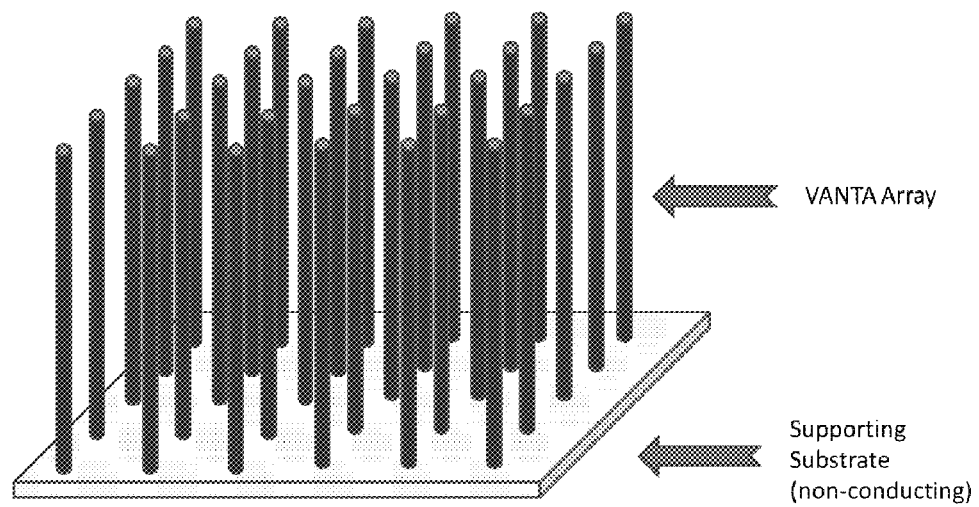
FIGS. 3A and 3B are schematic views showing how a VANTA film can be utilized as the sensor architecture.
Figure 3B:
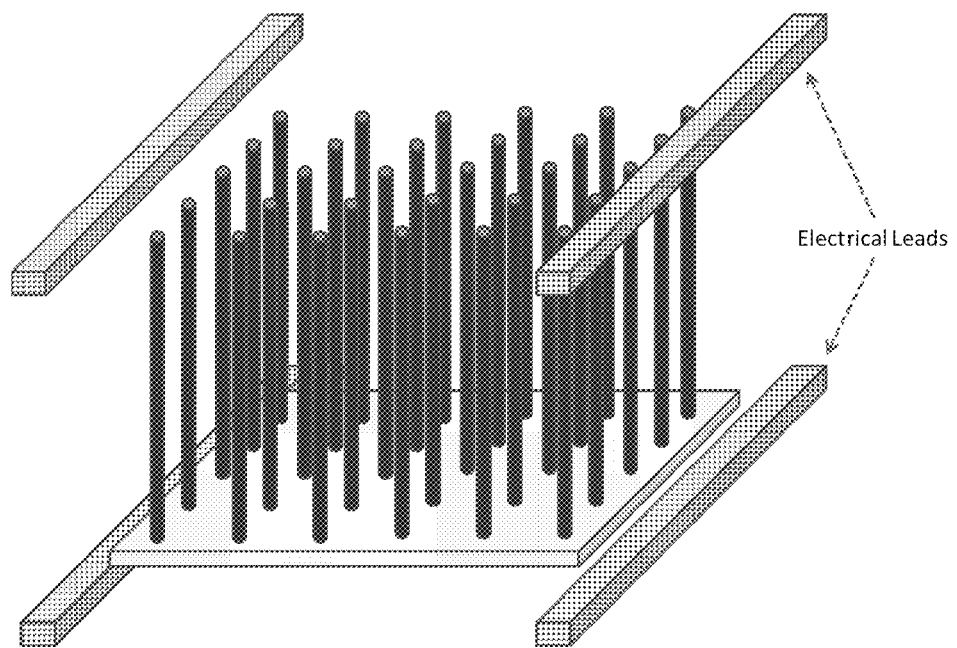
Figure 5:
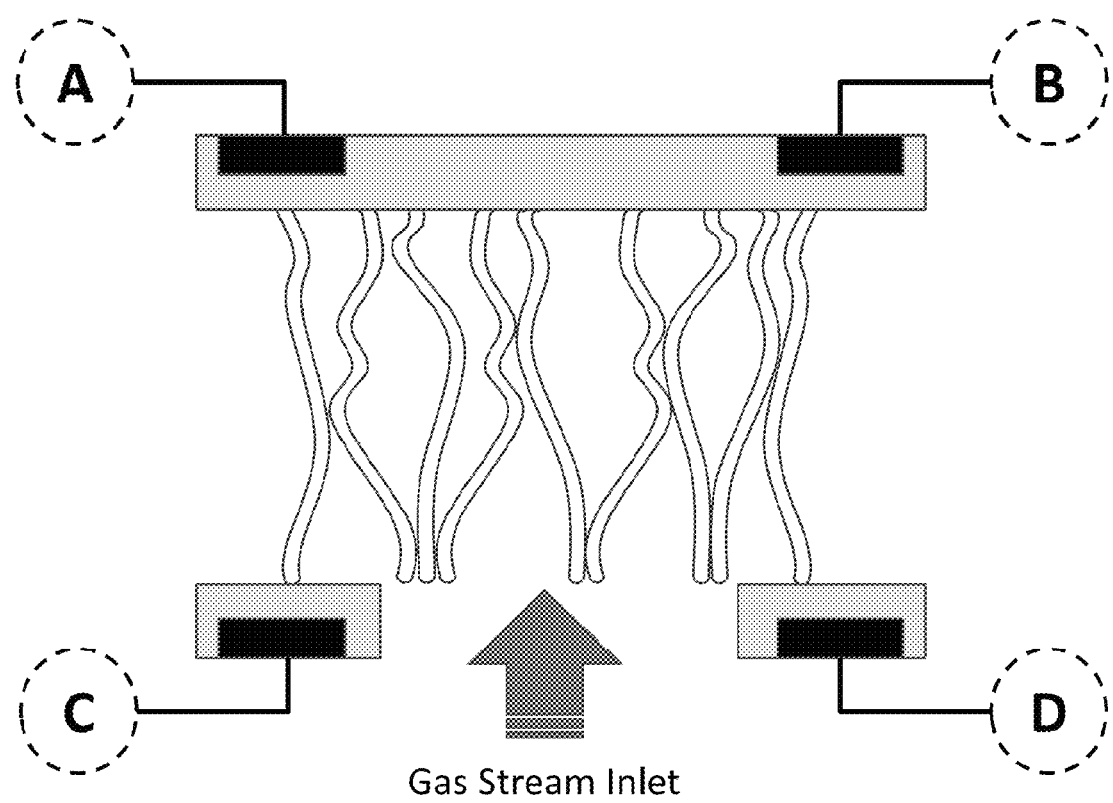
FIG. 5 is a schematic view showing further aspects of the side-to-side junctions of a VANTA structure.

In a particular embodiment, a VANTA film will be utilized as the sensor architecture with four electrical contact leads placed in such a way as to form capacitive contact with the VANTA architecture such these leads are parallel in orientation and equivalent to four edges of a square cuboid with a geometry such that they couple (capacitively) primarily to the VANTA (rather than each other). This arrangement is illustrated in FIGS. 3A & 3B below. (*Note: not completely representative of VANTA architecture and in-particular fails to represent the side-to-side junctions of the VANTA structure—this is represented more clearly in FIG. 5 which shows a side view of such an architecture). In a typical embodiment, this entire architecture will be enclosed in a Faraday cage to prevent extraneous electrodynamic couplings which would interfere with the sensing process.

Figure 4A:
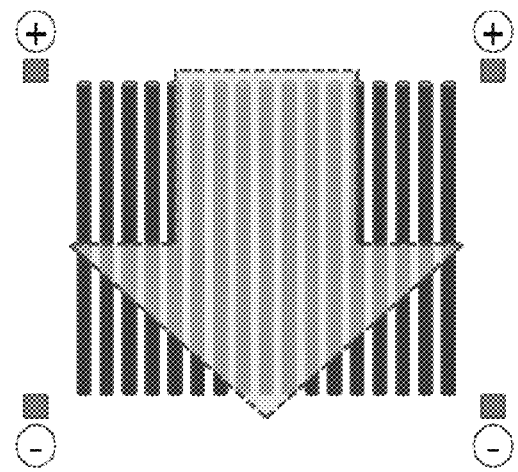
FIGS. 4A and 4B are schematic views showing how signals can be applied both axially through the VANTA-CNTs and transverse across VANTA-CNTs.
Figure 4B:
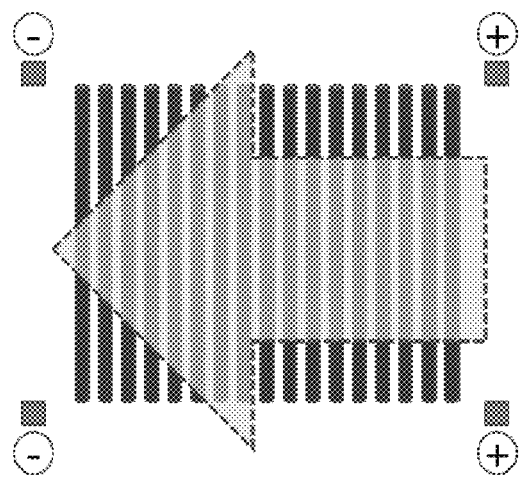

This arrangement enables signals to be applied both axially through the VANTA-CNTs and transverse across VANTA-CNTs as illustrated in FIGS. 4A & 4B respectively below.

Such a device may be fabricated by growing a VANTA on a non-conductive substrate with two conductive leads placed underneath the substrate and adhering a second structure in proximity over top of the VANTA wherein this structure possesses the other two conductive leads and enables gas transport to the VANTA for sensing. The VANTA growth may be accomplished by methods which are standard in the art. In some embodiments the VANTA may be grown on one substrate and then transferred to another substrate by methods common in the art.

In some embodiments it is advantageous to incorporate additional treatment steps into the processing of the VANTA array to modify functional device characteristics. Such treatment steps may be used individually or in conjunction may include:

Cleaning: A mild etching step may be incorporated during or after the growth process to remove non-CNT materials from the VANTA architecture. For instance, the VANTA may be exposed to a gas stream containing a mild oxidant such as water vapor typically at temperatures of about 500° C.-850° C. In some cases such etching procedures can also be utilized to remove or partially remove part of the "crust" layer typically present at the top of the VANTA architecture as it grows which which can significantly alter the transverse conductivity characteristics of the CNT array architecture.

Coking: A treatment to deposit carbonaceous materials other than pristine nanotubes incorporated into the VANTA lattice may be incorporated during or after the growth process. For instance, after CVD growth of the VANTA while the sample is still at or near the growth temperature the gas stream composition may be modified to increase carbonaceous and soot formation (e.g. by increasing the carbon precursor/hydrogen ratio in the gas stream and reducing total flow rate).

"Stacked Layer" Growth: During the growth process, the growth conditions may be interrupted and reinstated to terminate a growing VANTA layer and nucleate a new VANTA layer underneath the first. This process may be carried out more than once to create several different "layers" of VANTA growth. When suitably chosen conditions are utilized to create these "stacked layers" these layers can be separated from one another using a transfer process to create multiple sensors from a single stack. Due to differences in nucleation and growth dynamics these different layers can be utilized to have different sensing functional response—for instance the "top" layer of the growth stack will often have a more significant "crust" which can significantly alter the transverse conductivity characteristics of the CNT array architecture.

Reactive damage (e.g. ozone, O2, etc.): The VANTA may be subjected to species that will chemically react with the CNT surface to create additional surface moieties that will alter the chemical and physical characteristics of molecular interactions and charge conduction. Common reactive conditions include the use of ozone, molecular oxygen, plasma excited reagents, etc.

Non-reactive Plasma damage: The VANTA may be subjected to conditions that will cause physical damage to the CNT surface in such a way as to alter the chemical and physical characteristics of molecular interactions and charge conduction. Common physical damage conditions include the use of high energy inert particle bombardment such as argon plasma treatment.

Microwave treatment: The VANTA may be subjected to microwave irradiation which is known in some cases to alter the VANTA architecture and in particular reduce the entangled "crust" layer.

Annealing: The VANTA may be subjected to conditions that will cause annealing and/or degassing of the architecture prior to the operation to remove interferent chemical species and/or physical lattice defects from the VANTA architecture In some embodiments this annealing step may be carried out in a reduced pressure environment.

Figure 6:
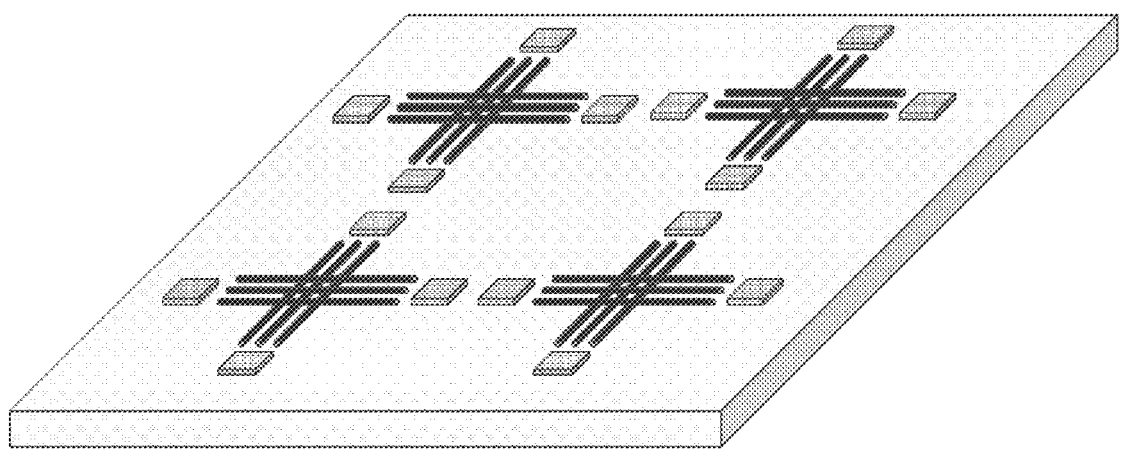
FIG. 6 is a schematic view showing exemplary architecture of a device comprising several sensor architectures functioning in parallel on the same substrate formed in accordance with the present invention.

In some embodiments, multiple, differentiated CNT-networks may be utilized in parallel to enhance selective detection. For instance, four VANTAs could be utilized wherein one is decorated with one sensitizer, another is decorated with a different sensitizer, another possesses nitrogen doping in its lattice, and the last is a traditional, unmodified CNT VANTA so that different chemical species will provide a discriminated electrical signature in each of these sensor architectures so that the sum of the four signals can better distinguish signals from different chemical signals. An example architecture of a device comprising several sensor architectures functioning in parallel on the same substrate (showing four crossed-arrays) is illustrated in FIG. 6.

In some embodiments such sensor devices may be incorporated into a circuit architecture possessing resonant characteristics. In such cases sensing events can be monitored via alterations in the resonance characteristics of the circuit. This can be utilized for wireless sensing architectures and in particular can reduce on-board power requirements for the sensor device.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for detecting and identifying a chemical species in an environment, said apparatus comprising:
    a plurality of carbon nanotubes arranged to form a network, said network comprising a plurality of inter-carbon nanotube junctions;
    a plurality of electrical contacts, each of said plurality of electrical contacts being connected to said network such that the anisotropic electrical characteristics of said network can be measured dynamically while said network is exposed to the environment;
    wherein said network possesses electrical anisotrophy such that the ratio of the number of inter-carbon nanotube junctions which must be traversed by current per length of said plurality of carbon nanotubes differs for different directions within said network along the path from one of said plurality of electrical contacts to another of said plurality of electrical contacts, and further wherein the electrical anisotrophy of said network changes when a chemical species is present in the environment.

2. A method for detecting and identifying a chemical species, said method comprising:
    providing apparatus for detecting and identifying a chemical species in the environment, said apparatus comprising:
        a plurality of carbon nanotubes arranged to form a network, said network comprising a plurality of inter-carbon nanotube junctions;
        a plurality of electrical contacts, each of said plurality of electrical contacts being connected to said network such that the anisotropic electrical characteristics of said network can be measured dynamically while said network is exposed to the environment;
        wherein said network possesses electrical anisotrophy such that the ratio of the number of inter-carbon nanotube junctions which must be traversed by current per length of said plurality of carbon nanotubes differs for different directions within said network along the path from one of said plurality of electrical contacts to another of said plurality of electrical contacts, and further wherein the electrical anisotrophy of said network changes when a chemical species is present in the environment;
    exposing said network to the environment such that a chemical species present in the environment can interact with said network;
    applying a series of electrical signals to said plurality of electrical contacts;
    measuring the anisotropic electrical characteristics of said network so as to determine if a chemical species is present in the environment.

* * * * *